United States Patent [19]

Resnick

[11] 4,374,854
[45] Feb. 22, 1983

[54] FUNGICIDAL SULFUR-CONTAINING PHENYL ESTERS AND MIXTURES THEREOF

[75] Inventor: Bruce M. Resnick, West Paterson, N.J.

[73] Assignee: GAF Corporation, New York, N.Y.

[21] Appl. No.: 250,809

[22] Filed: Apr. 3, 1981

[51] Int. Cl.³ .................... A61N 37/02; A61N 37/06; A61N 41/02
[52] U.S. Cl. .................................. 424/311; 424/303; 424/314
[58] Field of Search ....................... 424/314, 311, 303; 560/142

[56] References Cited
FOREIGN PATENT DOCUMENTS
740101 11/1955 United Kingdom .

Primary Examiner—Stanley J. Friedman

Attorney, Agent, or Firm—Marilyn J. Maue; J. Gary Mohr; Joshua J. Ward

[57] ABSTRACT

A broad spectrum sulfur-containing fungicide having the formula

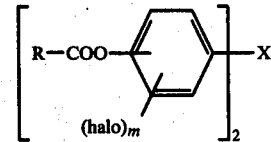

wherein X is sulfide, disulfide, sulfinyl, sulfonyl or sulfonate; m has a value of from 0 to 2; halo is fluorine, chlorine or bromine; and R is a radical having not more than 4 carbon atoms selected from the group consisting of alkenyl, haloalkenyl and haloalkyl; and the method of applying said esters to plants for control of fungi infestation.

10 Claims, No Drawings

FUNGICIDAL SULFUR-CONTAINING PHENYL ESTERS AND MIXTURES THEREOF

This invention relates to fungicides, and more particularly to broad spectrum biocides as eradicants and protectants against infestation by plant pathogens.

The effective mycological inhibition evidenced by differentiated chemical species is a complex function of a number of variables including specific activity, resistance to weathering, the type of plant treated, the degree of infestation and varying levels of phytotoxicity. Ecological considerations have barred the use of many effective fungicides because of their persistent residues and toxicity to humans by prolonged ingestation of food crops. To be commercially acceptable current fungicides must leave no toxic residue, they must be easily handled, operate consistently within a spray schedule and be economical to prepare. The foregoing requirements limit the selection of totally acceptable, effective fungicidal agents to a relatively small group of compounds. While many of the available materials comprise complex molecules of specific functionality, most are difficult or expensive to prepare and many of these materials, while effective against one fungicidal species, e.g. rusts, are not effective against other species, e.g. mildew or anthracnose. Such highly specialized fungicides necessitate the use of several sprays for controlling multifungicidal infestation; thus, increasing the amount of residue remaining on the plant or in the soil.

Accordingly, it is an object of the present invention to provide an effective broad spectrum fungicide for the control of mildews, rusts and anthracnose, suitable for application to plants and particularly suitable for food crops since, under normal conditions, these compounds leave no toxic residue.

It is another object of the present invention to provide effective mycological agents which are economical to prepare and convenient to use.

In accordance with the present invention, there is provided a broad spectrum, fungicidally effective compound having the formula

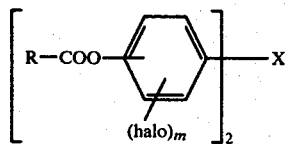

wherein X is sulfide (—S—), disulfide (—S—S—), sulfinyl (=SO), sulfonyl (=SO$_2$) or sulfonate

m has a value of from 0 to 2; halo is fluorine, chlorine or bromine and R is a radical having from 1 to 4 carbon atoms selected from the group consisting of alkenyl, haloalkenyl and haloalkyl; the acryloyl, chloroalkyl and bromoalkyl derivatives being preferred. The alkenyl and haloalkyl groups of the present compounds may be of a linear, branched or cyclic type. Alkenyl is intended to include multi olefinic unsaturation; however, mono-unsaturated and halosubstituted radicals having the functional moiety at their terminal carbon atoms are preferred. It is also to be understood that mixtures of the above sulfur containing ester compounds may be employed in the operation of the present invention.

In general the ester compounds of the present invention are prepared according to the processes described in British Pat. No. 740,101, Nov. 9, 1955; Vestn. Akad. Nauk Kaz. SSR 1971, 27(9) 53–9 by M. Kurmanaliev et al. and Makromol Chem. 1970, 136, 161–72 and 1969, 129, 125–36 by H. Kaemmerer et al. which publications are incorporated herein by reference. Specifically, the ester substituted compounds are easily and economically prepared by reacting an unsaturated acyl halide optionally substituted with halogen or a halocarboxylic acid halide with a diphenolic sulfide, sulfone, sulfine or sulfite in the presence of a base such as for example triethylamine, sodium carbonate, pyridine, etc. and a solvent selected from the group consisting of methylene chloride, toluene, xylene, benzene or a liquid aliphatic hydrocarbon such as heptane, octane, cyclohexane, or any other conventional inert organic solvent. The reaction can be carried out at a temperature of from about −25° C. to about 20° C. under atmospheric pressure for a period of from about 0.5 to about 2 hours. The organic layer is washed with water to extract the halide salt by-product, dried over a desiccant, e.g. magnesium sulfate, filtered to remove desiccant and vacuum distilled to remove solvent.

The product is recovered in a high yield and purity, for example, there is obtained at least 80% conversion of which about 90% is the desired product.

The corresponding haloalkyl esters are prepared by reacting the corresponding halogenated carboxylic acid halide with an above defined diphenol at a temperature of from about −25° C. to about 20° C. under atmospheric pressure. Other methods of preparation will become apparent to those skilled in the art from the above discussion of desirable compounds and the above described reaction conditions. Examples of suitable halogenated carboxylic acid halides include the chlorides or bromides of chloroacetic; 3-chloropropionic; dichloroacetic; 4-bromobutyric; 2,3-dichloropropionic; 3-trifluoromethyl propionic; 2,3,4-trichlorobutyric acids and other mono- and poly-halogenated carboxylic acid halides.

The phenolic reactants which can be used in the process for preparing the compounds of the present invention are those having the formula

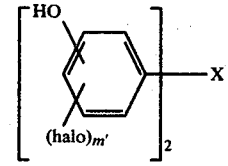

wherein X is bivalent and is selected from the group of

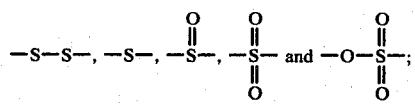

halo is as defined above and m' has a value of 1 to 2 and mixtures of said phenolic reactants.

Examples of the above phenolic reactants include bis(4-hydroxy-2-chlorophenyl)sulfide; bis(4-hydroxy-2- bromophenyl)sulfide; bis(4-hydroxy-2-fluorophenyl)-sulfide; bis(4-hydroxy-2,6-dichlorophenyl)sulfide; bis(2-hydroxyphenyl)sulfide; bis(5-hydroxy-2-chlorophenyl)-sulfide; bis(4-hydroxy-2,5-difluorophenyl)sulfide; bis(4-hydroxy-2,6-dibromophenyl)sulfide; bis(4-hydroxy-phenyl)sulfide; bis(3-hydroxyphenyl)sulfide; and the corresponding disulfides, sulfinyls, sulfonyls and sulfonates of the above sulfides and isomers and haloanalogs thereof.

The unsaturated acyl halide of the above reaction is defined as having the structure:

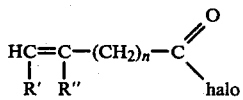

wherein R' is hydrogen, chlorine or bromine; R" is hydrogen or methyl; n has a value of 0 to 2 and halo is chlorine or bromine. Of this group acryloyl chloride and methacryloyl chloride are most preferred.

Representative of the products of this invention are included:
bis(4-acryloxy-2-chlorophenyl)sulfide;
bis(4-acryloxy-3-fluorophenyl)sulfide;
bis(4-acryloxy-2-bromophenyl)sulfide;
bis(4-acryloxy-2,6-dichlorophenyl)sulfide;
bis(4-acryloxy-2,5-dibromophenyl)sulfide;
bis(4-acryloxy-2,6-difluorophenyl)sulfide;
bis(4-acryloxy-phenyl)sulfide;
bis(4-methacryloxy-3-chlorophenyl)sulfide;
bis(4-methacryloxy-2-bromophenyl)sulfide;
bis(4-methacryloxy-2-fluorophenyl)sulfide;
bis(4-methacryloxy-2,6-dichlorophenyl)sulfide;
bis(4-methacryloxy-2,6-dibromophenyl)sulfide;
bis(4-methacryloxy-phenyl)sulfide;
bis(4-$\alpha$-chloroacetoxy-3-fluorophenyl)sulfide;
bis(4-$\alpha$-chloroacetoxy-2-bromophenyl)sulfide;
bis(4-$\alpha$-chloroacetoxy-2-chlorophenyl)sulfide;
bis(4-$\alpha$-chloroacetoxy-2,6-dichlorophenyl)sulfide;
bis(4-$\alpha$-chloroacetoxy-2,6-dibromophenyl)sulfide;
bis(4-$\alpha$-chloroacetoxy-phenyl)sulfide;
bis(4-$\alpha,\beta$-dichloropropanoyloxy-3-chlorophenyl)sulfide;
bis(4-$\alpha,\beta$-dichloropropanoyloxy-2,6-dichlorophenyl)-sulfide;
bis(4-$\alpha,\beta$-dichloropropanoyloxy-phenyl)sulfide;
bis(4-$\beta$-bromoacryloxy-2-bromophenyl)sulfide;
bis(4-$\beta$-bromoacryloxy-2,6-dibromophenyl)sulfide;
bis(4-$\beta$-bromoacryloxy-phenyl)sulfide;
bis 4,4'-(3,4-dichlorobutanoyloxy-2-chlorophenyl)sulfide;
bis 4,4'-(3,4-dichlorobutanoyloxy-2,6-dichlorophenyl)-sulfide;
bis 4,4'-(3,4-dichlorobutanoyloxy-phenyl)sulfide;
and the corresponding disulfides, sulfinyls, sulfonyls, and sulfonates of the above sulfides and isomers and haloanalogs thereof.

The esters of the present invention effect inhibition of widely variant plant pathogens and may be generally used in the control of infestations on many species of plants by application prior to infestation as a protectant or after infestation to retard established growth. Although the present products may be applied in full strength, directly to a plant or plant part, for economy and better distribution, the product is preferably applied in diluted form as a liquid solution or dispersion or as a particulate solid or a dust. Suitable liquid carriers for the present products include water and organic solvents such as isopropanol, ethylene glycol, acetone, benzene, toluene, polyethylene glycol, polypropylene glycol, and other conventional inert carriers. Exemplary of the solid carriers suitably employed with the present products are talc, bentonite, diatomaceous earth clays, and the like.

The concentration of the active fungicide varies with the species of plant treated, the mycological species sought to be controlled, climatic conditions and the particular fungicide employed; however, the present products are usually applied in a concentration of between about 5 and about 300 parts per million, preferably between about 20 and about 200 parts per million, applied to provide coverage of from about 1 to about 30 lbs. per acre, preferably about 3 to about 25 lbs. per acre. In certain cases involving a persistent or heavy fungicidal infestation, it may be desirable to employ solutions up to 500 ppm of the present fungicides.

The fungicidal compositions of the present invention may also be applied to or compounded in or with other substrates susceptible to fungal infestation including wood, paper, leather textiles etc.; however their preferred utility is expressed in the field of agriculture, and particularly in the control of plant pathogens as by foliar application as a liquid spray or dust either to growing crops or processed agricultural products, e.g. picked fruit or vegetables. The present products may also find utility as bacteriocides in household or commercial washing or cleansing solutions.

The fungicidal products can be formulated and applied with carrier or they may be incorporated in available formulations containing other agriculturally active agents such as plant growth regulators, insecticides, fertilizers or herbicides, as are presently marketed. In all cases, the fungicidal compositions of this invention are used in fungicidally effective amounts in the desired formulation. Liquid compositions containing the present fungicides can be applied to plants by spraying to drench, by misting or by immersing picked fruit or vegetables in a fungicidal solution. Also wrappings for fruits and vegetables can be impregnated with the present fungicide/carrier composition to prevent rot or decay during shipment and distribution.

If desired, the present fungicidal compositions may include any of the conventional adjuvants such as surfactants, thickening agents, or sticking agents.

Having generally described the present invention, reference is now had to the accompanying examples which illustrate preferred embodiments but which are not to be construed as limiting the scope of the invention as set forth in the foregoing description and in the appended claims. All amounts and proportions recited in the following examples are by weight unless otherwise indicated.

EXAMPLE 1

Powdery mildew. The bean powdery mildew is an obligately parasitic fungus that must be transferred directly from infected plants to healthy plants in a relatively dry environment. In the present tests, healthy young bean plants with fully expanded primary leaves in 2½" pots were placed for 2 days on a greenhouse bench between two rows of infected plants covered with a mass of white, powdery conidia, and exposed to a shower of conidia.

Plants with incipient infection were atomized while rotating on a turntable with an aqueous solution of 250 ppm of test material shown in Table I and the soil was drenched with 21 ml of a 520 ppm solution (at a rate equivalent to 25 lb/acre). The treated plants were then returned to the greenhouse bench near infected plants. After 7 days observations were made on the eradication of established infection present on the primary leaves at the time of spraying. The plants were reexamined 7 days later for infection on new growth as well as on the primary leaves to determine residual and systemic effects on the fungus. On both occasions the leaves are rated as % control of mildew.

TABLE I

| | | % Control of Infestation | |
|---|---|---|---|
| Test Compound | Chemical Name | Arrested (14 Days) | Eradicated (7 Days) |
|  | 4,4'-diacryloxy-diphenyl sulfide | 100 | 40 |
| 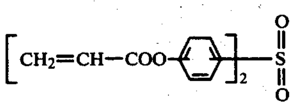  | 4,4'-diacryloxy-diphenyl sulfone | 70 | 40 |

EXAMPLE 2

Bean rust (Uromyces phaseoli) is representative of a large number of obligate parasites whose prolificacy in generating new parasitic races has frequently frustrated efforts to control them by breeding for disease resistance. The present tests were made with separate aqueous solutions each containing 260 ppm the compounds shown in Table II on Pinto beans grown in 2.5 inch pots for 9 to 12 days by a combination of foliage spray and systemic protection from soil applications. In the test 21 ml of a 520 ppm formulation (equivalent to 25 lb/acre) was poured on the surface of the soil. At the same time the foliage was sprayed with 100 ml of the aqueous solutions containing 260 ppm of the compounds shown in Table I while plants were rotating on a turntable. After the spray deposit had dried, the plants were atomized with a suspension of uredospores (summer spore stage) and placed in a moist chamber at 70° F. for 24 hours. After 7 to 9 days the severity of pustule formation was rated in % control, as compared to untreated controls. The results are reported in following Table II.

TABLE II

| Test Compound | Chemical Name | % Control of Rust Infestation |
|---|---|---|
|  | 4,4'-di-3-chloropropanoyloxy diphenyl sulfone | 100 |
| 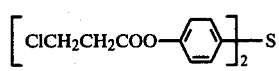  | 4,4'-di-3-chloropropanoyloxy diphenyl sulfide | 100 |
| 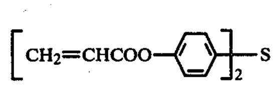  | 4,4'-diacryloxy diphenyl sulfide | 100 |
| 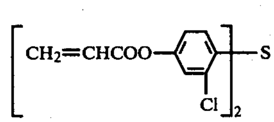  | 4,4'-diacryloxy-2,2'-dichlorophenyl sulfide | 90 |
| 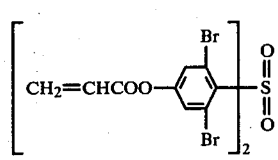  | 4,4'-diacryloxy-2,2',6,6'-tetrabromophenyl sulfone | 90 |
| 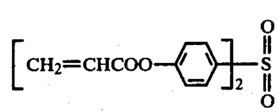  | 4,4'-diacryloxy diphenyl sulfone | 90 |
| 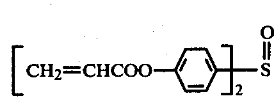  | 4,4'-diacryloxy diphenyl sulfoxide | 100 |

TABLE II-continued

| Test Compound | Chemical Name | % Control of Rust Infestation |
|---|---|---|
| [CH₃CH=CHCOO—⟨phenyl⟩—]₂S | 4,4'-di-2-butenyloxy diphenyl sulfide | 90 |
| [CH₃CH=CHCOO—⟨phenyl⟩—]₂S(=O) | 4,4'di-2-butenyloxy diphenyl sulfoxide | 100 |
| [CH₃CH=CHCOO—⟨phenyl⟩—]₂S(=O)₂ | 4,4'-di-2-butenyloxy diphenyl sulfone | 90 |
| [ClCH₂COO—⟨phenyl⟩—]₂S | 4,4'-dichloroacetoxy diphenyl sulfide | 50 |

The above compounds did not exhibit systemic activity; hence; foliar application is recommended.

EXAMPLE 3

Cucumber anthracnose (*Colletotrichum lagenarium*) is a representative of leaf blights caused by the *Fungi Imperfecti*. Tests were made on cucumber plants grown in 2.5 inch pots for 9–12 days by a combination of foliage spray. In the test, the foliage was sprayed with 100 ml of a 250 ppm aqueous formulation of the compounds reported in Table III as described below. After the spray deposit had dried, the treated plants were inoculated with a suspension of anthracnose conidia in water and placed in a moist chamber at 24° C. for 24 hours. Four days after inoculation, the number of lesions were counted, and % control reported.

TABLE III

| Test Compound | % Control of Anthracnose Infestation |
|---|---|
| [ClCH₂CH₂COO—⟨phenyl⟩—]₂S(=O)₂ | 100 |
| [ClCH₂CH₂COO—⟨phenyl⟩—]₂S | 100 |
| [CH₂=CHCOO—⟨phenyl⟩—]₂S | 100 |
| [CH₂=CHCOO—⟨phenyl⟩—]₂S(=O)₂ | 100 |
| [CH₂=CHCOO—⟨phenyl⟩—]₂S(=O) | 100 |
| [CH₃CH=CHCOO—⟨phenyl⟩—]₂S | 10 |
| [ClCH₂COO—⟨phenyl⟩—]₂S | 100 |

When 4,4'-diacryloxy-2,2'-dichlorophenyl- or 4,4'-diacryloxy-2,2'-dichlorophenyl-sulfones are substituted in this example, at least 70% control of anthracnose is obtained.

EXAMPLE 4

The general procedures described the above examples 2 and 3 were repeated for test compounds at varying concentrations reported in Table IV. Control of the rust and anthracnose, at various fungicidal concentration levels are reported in following Table IV.

TABLE IV

| Test Compound | Pathogen | % Control of Pathogen | | | | |
|---|---|---|---|---|---|---|
| | | 130 ppm | 65 ppm | 33 ppm | 16 ppm | 8 ppm |
| [ClCH₂CH₂COO—⟨phenyl⟩—]₂S(=O)₂ | R* | 90 | 70 | 50 | — | — |
| | A* | 80 | 80 | 40 | — | — |
| [ClCH₂CH₂COO—⟨phenyl⟩—]₂S | R | 70 | 30 | 20 | — | — |
| | A | 0 | 10 | 50 | — | — |
| [CH₂=CHCOO—⟨phenyl⟩—]₂S | R | 100 | 90 | 100 | 70 | 40 |
| | A | 100 | 100 | 100 | 70 | 30 |

TABLE IV-continued

| Test Compound | Pathogen | % Control of Pathogen | | | | |
|---|---|---|---|---|---|---|
| | | 130 ppm | 65 ppm | 33 ppm | 16 ppm | 8 ppm |
| $\left[CH_2=CHCOO-\underset{}{\bigcirc}\right]_2 \underset{O}{\overset{O}{\underset{\|}{\overset{\|}{S}}}}$ | R | 90 | 90 | 90 | 70 | 40 |
| | A | 100 | 90 | 50 | — | — |
| $\left[CH_2=CHCOO-\underset{}{\bigcirc}\right]_2 \overset{O}{\underset{\|}{S}}$ | R | 90 | 70 | 30 | — | — |
| | A | 50 | 20 | 0 | — | — |
| $\left[ClCH_2COO-\underset{}{\bigcirc}\right]_2 S$ | R | — | — | — | — | — |
| | A | 100 | — | — | — | — |

*R = rust; A = anthracnose

Of the above compounds, the sulfide and the sulfone of diacryloxyphenyl, both at a concentration level of 65 ppm, additionally provided about 50% control of powdery mildew on bean plants.

As shown in the above tables, the most preferred concentration levels of the present fungicidal compounds fall within the range of between about 30 and about 300 ppm. Other compounds, included within the scope of the present invention may require higher concentrations to achieve maximum effectiveness, e.g., concentrations of up to about 500 ppm. The present compounds are advantageously used on edible crops since they leave no toxic residue and have no systemic effect beyond 2 weeks following application. These properties make the present fungicidal compounds ideal for treatment of picked fruit and vegetables to prevent spoilage in shipment and storage.

It is to be understood that many variations and modifications of the above examples will become apparent to those skilled in the art and are considered to be in the scope of the invention. For example, the present fungicides may be incorporated into solid carriers such as clay, talc, pumice, or bentonite to provide compositions which may be applied either to infested areas on the plant or to areas which may be subjected to infestation. They may also be dissolved in liquified gases such as methyl chloride and applied as aerosol sprays containing the solution. Also, any of the corresponding mono- or di-hydroxy phenyl sulfides, sulfones, sulfines or sulfites can be substituted in the above examples to provide similar fungicidal control.

I claim:

1. The method of inhibiting growth of fungi which comprises exposing said fungi to a growth inhibiting quantity of a compound having the formula

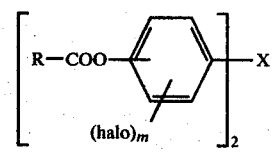

wherein X is —S—, —SS—, —SO—, —SO$_2$— or —SO$_3$— m has a value of from 0 to 2; halo is fluorine, chlorine or bromine and R is a radical having not more than 4 carbon atoms selected from the group consisting of alkenyl, haloalkenyl and haloalkyl; and mixtures of said compounds.

2. The method of claim 1 wherein said compound is applied to a plant in an amount sufficient to prevent or control fungus infestation.

3. The method of claim 2 wherein RCO$_2$— of the compound is an acrylate radical.

4. The method of claim 2 wherein RCO$_2$— of the compound is a methacrylate radical.

5. The method of claim 2 wherein R of the compound is a haloethyl group and halo is chlorine or bromine.

6. The method of claim 3 wherein the compound is a sulfone.

7. The method of claim 3 wherein the compound is a sulfide.

8. The method of claim 2 wherein the compound is employed with an aqueous carrier in a concentration of between about 30 and about 500 ppm.

9. The method of claim 8 wherein the fungus is plant rust.

10. The method of claim 8 wherein the fungus is anthracnose.

* * * * *